United States Patent [19]

Lundberg

[11] Patent Number: 5,318,010
[45] Date of Patent: Jun. 7, 1994

[54] MEDICAL INSTRUMENT

[75] Inventor: Hans Lundberg, Ebeltoft, Denmark

[73] Assignee: Danvag Ltd., Great Harwood, United Kingdom

[21] Appl. No.: 730,781

[22] PCT Filed: Jan. 29, 1990

[86] PCT No.: PCT/GB90/00128

§ 371 Date: Sep. 1, 1992

§ 102(e) Date: Sep. 1, 1992

[87] PCT Pub. No.: WO90/08499

PCT Pub. Date: Aug. 9, 1990

[30] Foreign Application Priority Data

Jan. 27, 1989 [GB] United Kingdom ............... 8901877

[51] Int. Cl.⁵ .............................................. A61B 1/32
[52] U.S. Cl. ...................................... 128/17; 128/20
[58] Field of Search ............... 128/20, 3, 10, 11, 17, 128/18; 606/191, 198

[56] References Cited

U.S. PATENT DOCUMENTS

| | | | |
|---|---|---|---|
| 3,246,646 | 4/1966 | Murphy, Jr. | 128/17 |
| 3,716,047 | 2/1973 | Moore et al. | 128/18 |
| 3,750,651 | 8/1973 | Brammer | 128/20 |
| 3,762,400 | 10/1973 | McDonald | 128/18 |
| 3,815,585 | 6/1974 | Fiore | 128/17 |
| 3,817,242 | 6/1974 | Uddenberg | 128/20 |
| 3,851,642 | 12/1974 | McDonald | 128/18 |
| 4,638,792 | 1/1987 | Burgin | 128/18 X |
| 5,231,973 | 8/1993 | Dickie | 128/17 |

FOREIGN PATENT DOCUMENTS

1061259 3/1967 United Kingdom .

Primary Examiner—Stephen R. Crow
Assistant Examiner—Donna L. Maraglio
Attorney, Agent, or Firm—Biebel & French

[57] ABSTRACT

An instrument for vaginal inspection or exploration consists of separate speculum and depressor components, each molded from plastic material. The handles of the components are adapted to be releasably interfitted in a dovetail manner to form a unitary handle, with the handles being longitudinally slidable relative to each other to adjust the separation between the speculum and depressor blades. The dovetail arrangement includes toothed locking flanges on the depressor handle which releasably cooperate with teeth on the sides of the speculum handle. By depressing a transverse web portion or button, the flanges are flexed apart to allow longitudinal adjustment between the handles, using one hand only. The depressor handle includes an intermediate member connected to the depressor blade. This intermediate member is of an arcuate, laterally offset configuration so as to provide unobstructed access to the space between the blades in the longitudinal direction of the blades.

20 Claims, 4 Drawing Sheets

MEDICAL INSTRUMENT

This invention relates to a medical instrument, for example an instrument for use in vaginal inspection and/or exploration comprising elements for separating mucous vaginal membranes and for seizing the region to be inspected and/or acted on, which enables the doctor to guide said instrument with either one or two hands.

A vaginal inspection and/or exploration is often both physically and psychologically distressing for the women in question. Furthermore, since no two females are anatomically identical, individual treatment requires the application of a highly adjustable instrument. In addition to all the demands made by doctors and patients on its design and clinical adjustability, the cost of said instrument must be low enough to allow the instrument to be disposable, particularly in view of today's extremely serious sexually transmitted diseases Instruments for vaginal inspection and/or exploration in present use vary considerably in design and, unfortunately, application is often impractical and complicated for the doctor and painful for the patient.

The most simple conventional type of vaginal instrument (speculum) is a relatively simple bent-up instrument, of which one or sometimes both ends consist of tongued, crescent-section elements for separating mucous vaginal membranes, in order to permit viewing the sexual organ to be examined, e.g. cervix, uteri and portio vaginalis, with the aid of a "spoon-shaped" instrument (depressor). To insert the above-mentioned instruments, and maintain them in the required position, the doctor has to use both hands. If, after successful insertion of the instruments, knives, scissors, etc., are required (cellular tests are almost always carried out at this point), the handling of both speculum and depressor must be transferred to an assistant or nurse. This procedure is generally rather clumsy and awkward, and freedom of movement is hampered by the need for hands and arms to be centred around the area of which a good view is necessary in order to perform the operation in question.

One way of partially solving the problem of space is to use a so-called interlocking speculum which incorporates body-engageable elements resembling an elongated duck's bill. These elements, which comprise two crescent-section tongues, joined together by means of a hinge device, are inserted into the vagina and, provided the correct tongue width is chosen, said instrument can be adjusted to a suitable opening for the woman in question by means of a locking mechanism. All instruments of this type are somewhat clumsy and cause unnecessary discomfort. Furthermore, due to the hinge mechanism itself, said instrument, even when greatly dilated, allows very little room for insertion of any surgical instrument, and obstructs the view necessary to perform an operation. The sole advantage of such a "duckbill" speculum is that its application requires one hand only. However, this instrument is seldom used due to the above-mentioned disadvantages, and also due to high manufacturing costs.

Another type of interlocking speculum which has been proposed, in U.S. Pat. Nos. 3,815,585 and 3,750,651, and GB-A-1,061,259, incorporates duckbilled elements which are longitudinally slidable relative to each other.

It is an object of the present invention to provide an improved medical instrument, generally of the type disclosed in U.S. Pat. Nos. 3,815,585 and 3,750,651.

According to the present invention, there is provided an instrument for enabling the inspection and/or exploration of a body cavity or the like, comprising a first component, having a first elongate hand-grip member, and a first elongate body-engageable element, the first hand-grip member, in use, being connected to the first body-engageable element, and being adapted to be grasped in one hand for manipulation of the first body-engageable element, a second component, separable from the first component, having a second elongate hand-grip member, and a second elongate body-engageable element, the second hand-grip member, in use, being connected to the second body engageable element, and being adapted to be grasped in one hand, independently of the first hand-grip member, for manipulation of the second body-engageable element independently of the first body-engageable element, one hand-grip member being releasably slidably receivable in a longitudinal substantially straight channel defined by the other hand-grip member with the cooperating surfaces of the channel and of said one hand-grip member forming guide means operable to constrain the hand-grip members to extend, and to be relatively manually displaceable, in a first common direction, along a substantially rectilinear path, to relatively adjust the separation between the first and second body-engageable elements, the guide means being associated with resilient locking means operable to releasably lock the hand-grip members in an adjusted position, the guide means also being associated with retaining means operable to retain the hand-grip members interconnected to form an integrated handle adapted to be grasped in one hand with the manipulation of both body-engageable elements, and the relative separational adjustment, being effected by said one hand, the side walls of the channel in said other hand-grip member, and the sides of one said hand-grip member with which the side walls are cooperable, being provided with said retaining means, which retaining means comprise longitudinally extending, internal undercut regions in the side walls in which longitudinally extending rib portions on the sides are slidably engageable, said undercut regions and rib portions being adapted to permit the hand-grip members to be assembled and disassembled when the body-engageable elements are located close together, each body-engageable element, in use, extending at an angle to its associated hand-grip member whereby, when the hand-grip members are interconnected, the body-engageable elements are constrained to extend generally in a second common direction, at an angle to said first common direction, with the first body-engageable element interposed between the second body-engageable element and the first hand-grip member in the direction of elongation of the integrated handle, and the second hand-grip member including an intermediate member, the second hand-grip member, in use, being connected to the second body-engageable element by the intermediate member, and the intermediate member being offset laterally relative to the body-engageable elements to provide access, in the direction of elongation of the elements, past the intermediate member to the space between the elements.

In one embodiment, as applied to an instrument for use in vaginal inspection and/or exploration, the first component is a speculum, the first body-engageable element being a speculum element for separating mucous vaginal membranes. The second component is a depressor, the second body-engageable element being a depressor element for seizing the region to be inspected and/or acted upon. Both elements form angled extensions, for example generally perpendicular extensions, of associated matchingly formed hand-grip handle members which are capable of being releasably interconnected, for example resiliently releasably interconnected in side-by-side relation, to form an integrated or composite handle. The hand-grip handle members are provided with mutually interlocking longitudinal guide means to retain the integrity of the composite handle, while permitting longitudinal sliding movement between the hand-grip handle members, thus enabling the distance between the speculum and depressor elements to be varied.

A locking arrangement is operable to releasably lock the handle members, and therefore lock the speculum and depressor elements apart in any required adjusted position, the locking arrangement being readily manually releasable to allow the elements to be moved back towards each other for ready removal of the instrument. The laterally offset intermediate member, which joins the depressor element to its handle member, is preferably of arcuate or part-annular shape, to provide an effectively unobstructed line of sight along the elements.

In the instrument embodying the invention, one or both handle members are configured as outwardly open generally rectangular or box-section channels. The interlocking and guiding means comprise matching portions of the side walls or flanges of the channels which are capable of positive engagement when one handle member is fitted into the channel in the other member. The side walls or flanges may have dovetailed or undercut sections, provided with tooth means, at least towards the inner or proximal ends of the handle members, i.e. the ends nearest to the speculum and depressor elements. The tooth means of both handle members are resiliently interengageable in such a manner that they normally lock the handle members against relative sliding movement, at least in the direction which would allow the speculum and depressor elements to move closer together.

The front or foremost handle member, i.e. the handle member nearest to the patient and farthest from the doctor, may be the first handle member associated with the speculum (first) element and the rearmost handle member, i.e. the handle member farthest from the patient and nearest to the doctor, may be the second handle member associated with the depressor (second) element. The rearmost handle member may be provided with an arch-shaped web portion in the region of the tooth means on the flanges of that handle member, which is resiliently depressible to force apart and disengage or partly disengage the tooth means by thumb pressure to permit simultaneous adjustment of the handle members and elements with the thumb (one-hand operation or control). Additionally or alternatively, flanges may be provided on the rearmost handle member which are extended locally into ears or grips in the region of the tooth means, which may be pinched together to force apart and at least partially disengage the tooth means with one hand, while holding the handle member steady with the other hand (two-hand operation or control).

Each handle member and associated body-engageable element may be moulded, for example injection moulded, from a synthetic plastics material. The handle members including the intermediate member which may also be channel section, may be reinforced by ribs or webs moulded integrally with the bases and/or side walls or flanges of the channels, the ribs or webs forming, for example, a parallel or criss-cross pattern.

The handle members may be formed integrally with their associated speculum and depressor elements, or may be formed separately therefrom and may be capable of accommodating blade or tongue-like elements of different widths and/or shapes. A slit- and tongue snap-action connection may be provided between the handle member and the speculum element and/or depressor element.

The instrument embodying the invention offers significant advantages to both doctor and patient. Furthermore, the instrument can be manufactured relatively cheaply and easily, and is therefore particularly suitable for use as a disposable instrument.

In order that the invention may be more readily understood, reference will now be made to the accompanying drawings, in which.

The instrument shown in FIGS. 1 to 4 comprises two main components, namely a speculum component 1 and a depressor component 4, each integrally moulded, for example injection moulded, from a rigid but resilient synthetic plastics material such as polythene or polyvinyl chloride. The speculum component 1 comprises a speculum spoon, tongue or blade 2 which forms a generally right-angled extension at the proximal end of a hand-grip or handle member 3. The depressor component 4 comprises a depressor tongue or blade 5 which forms a generally right-angled extension at the proximal end of a hand-grip or handle member 6, and is connected to the hand-grip or handle member 6 by a laterally offset, arcuate, intermediate member 8.

Figures 1, 2:
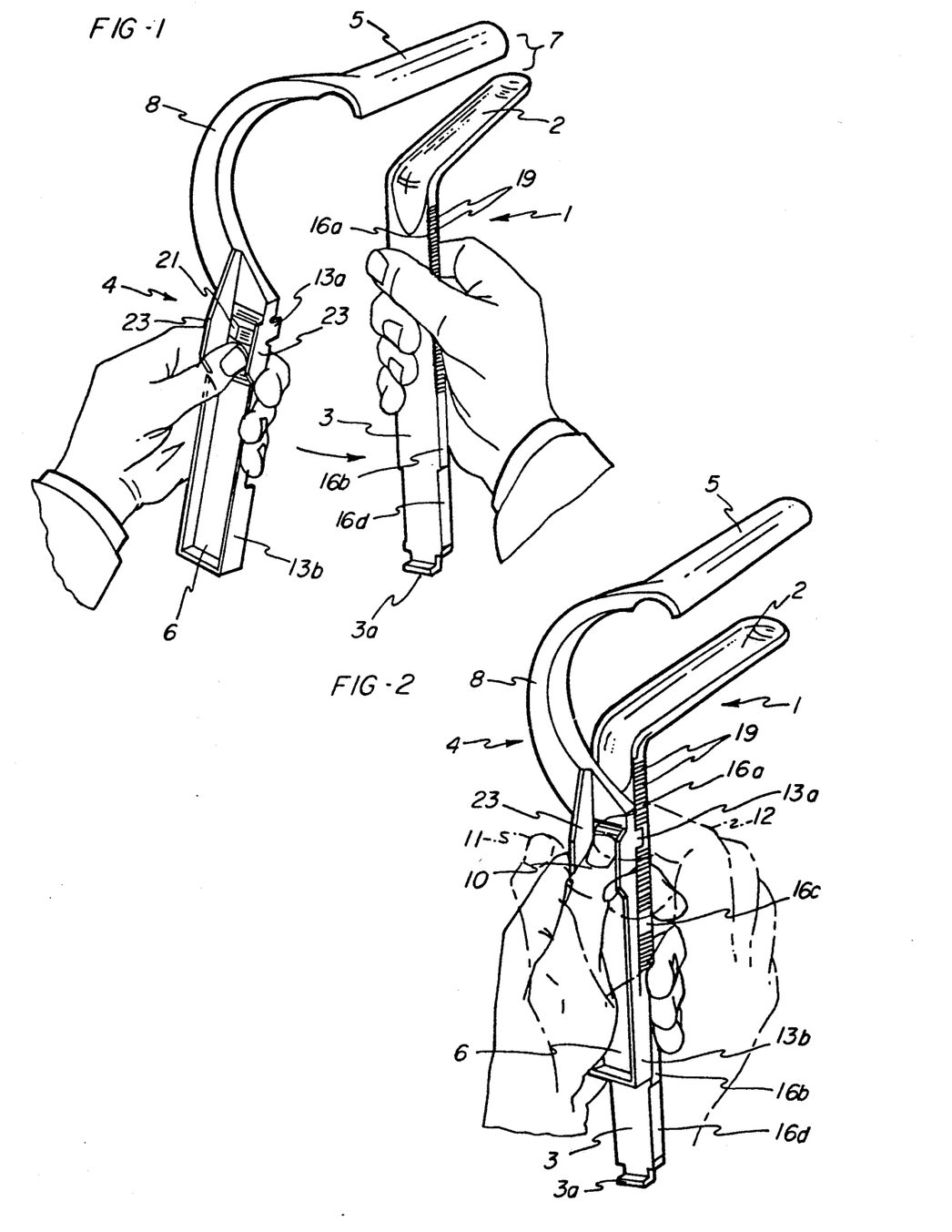
FIG. 1 is a perspective view of one embodiment of instrument, illustrating the "orientation step" during which the doctor applies both hands to the handle members of the speculum and depressor components.
FIG. 2 is a similar view illustrating the interlocking of the speculum and depressor handle members to form one instrument.

The speculum and depressor components, which are shown separated in FIG. 1 may be clipped together by means of their handle members 3 and 6 as shown in FIG. 2. When so interconnected, the handle members 3 and 6 form a unitary, composite or integrated handle in which the handle members may slide axially or longitudinally relative to each other to adjust the distance between the speculum and depressor blades 2 and 5.

Figure 3:
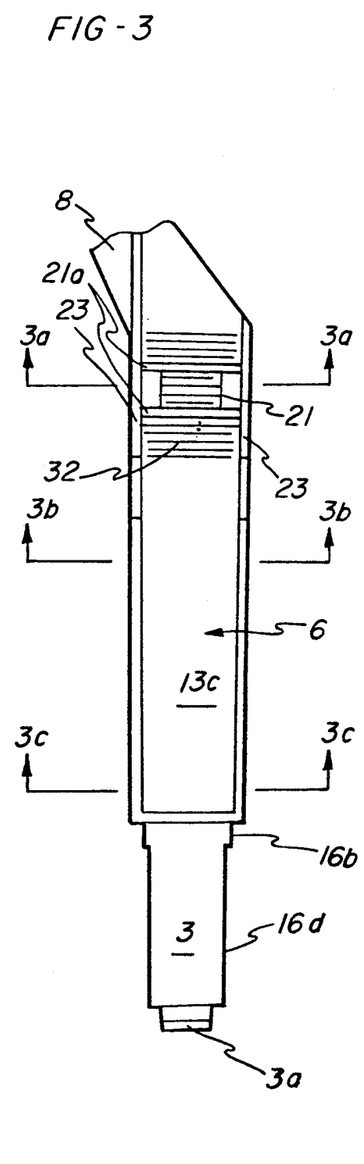
FIG. 3 is a fragmentary plan view of the interlocked handle member - guiding means, grip and orientation mechanism.
Figure 3A:
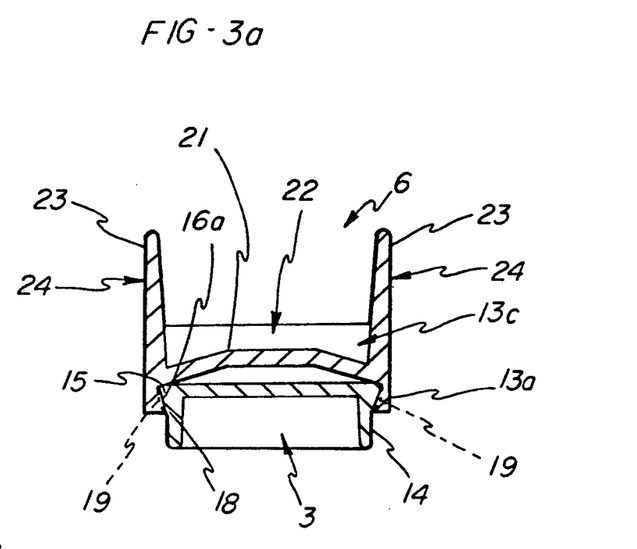
FIGS. 3a, 3b and 3c are cross-sectional views taken, respectively on the lines 3a—3a, 3b—3b and 3c—3c in FIG. 3.
Figure 3B:
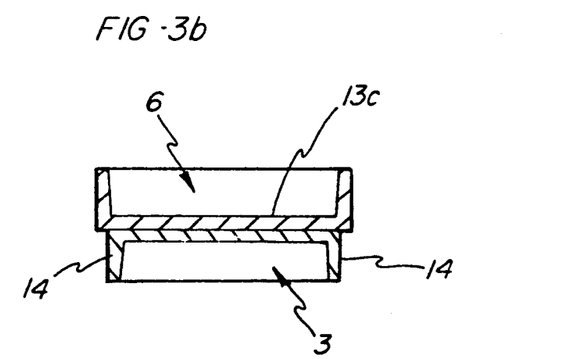
Figure 3C:
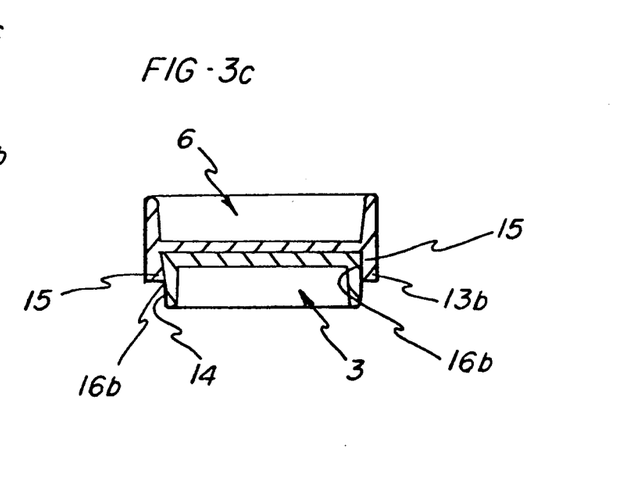

As will be apparent from FIGS. 3a, 3b and 3c, the handle members 3 and 6 are in the form of elongate channel members of generally rectangular cross-section. The depressor handle member 6 is double-channelled, i.e. of generally rectangular or "H" cross-section, and as viewed in these Figs, the handle member 3 fits into and is slidable along and within the lower channel in the handle member 6.

The side walls or flanges of the speculum handle member 3 are formed externally with inclined or wedge shaped, longitudinally extending, proximal and intermediate rib portions 16a and 16b (see FIGS. 2, 3a and 3c), and with intermediate and distal gaps 16c and 16d which are devoid of such rib portions (see FIGS. 2 and 3b). At least the proximal rib portions 16a are formed with serrations or teeth 19. At its distal end, the handle member 3 is provided with a stop 3a.

Figures 4, 4A:
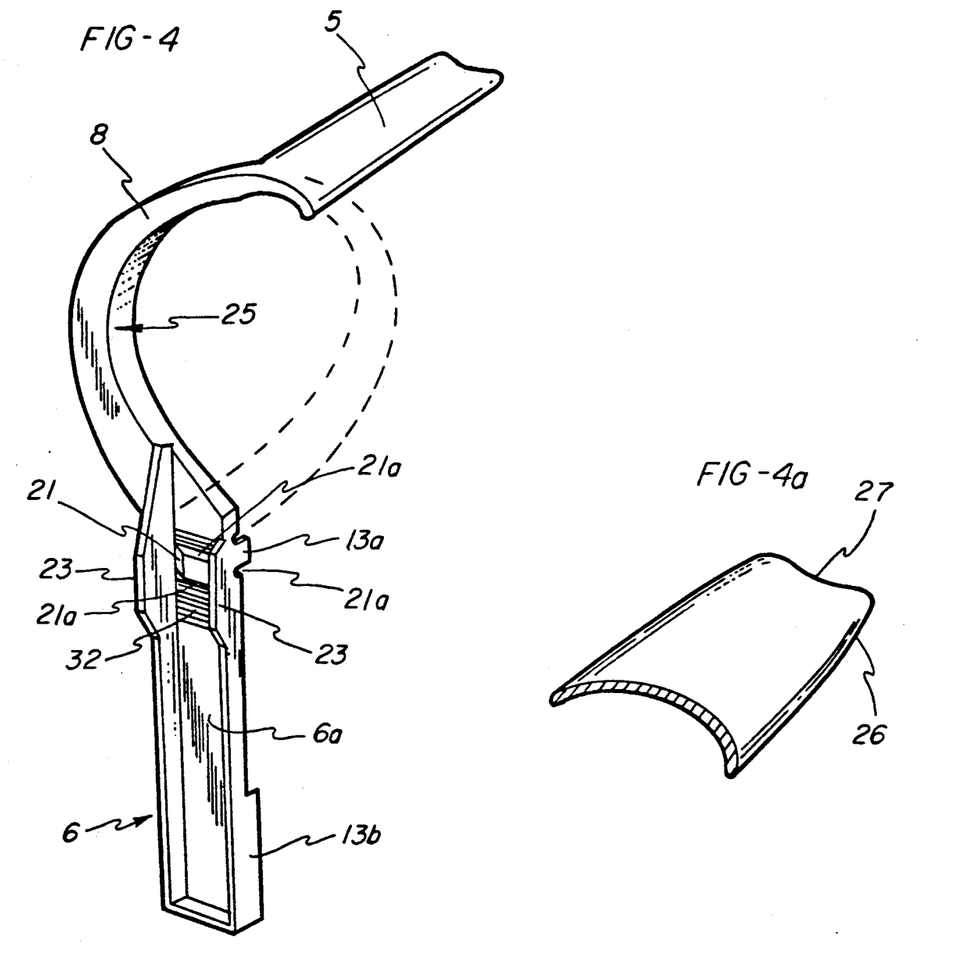
FIG. 4 is a fragmentary perspective view, on an enlarged scale, of the depressor shown in the preceding Figs. A right-handed design is shown in full lines and a left-handed design is shown in broken lines.
FIG. 4a is a fragmentary perspective view, on an enlarged scale, of the tip of the depressor element shown in FIG. 4.

The side walls or flanges of the lower channel in the depressor handle member 6 are interrupted to leave proximal and distal side wall or flange portions 13a and 13b respectively (see FIGS. 1, 2 and 4). As shown in FIGS. 3a and 3c these flange portions have undercut regions 15 which are cooperable with the rib portions 16a and 16b on the speculum handle member 3 to retain the handle members slidably assembled together. The flange portions 13a and 13b are so dimensioned and positioned that, when the handle members are brought together, represented by the unlabelled arrow in FIG. 1, with the distal end of the depressor handle member 6 adjacent the stop 3a, the flange portions 13a and 13b align with the gaps 16c and 16d, allowing the handle member 3 to fit into the channel in the handle member 6 in a direction perpendicular to the longitudinal direction of the handle members (i.e. in a direction corresponding generally to the longitudinal direction of the blades 2 and 5). Subsequent longitudinal sliding movement of the handle member 6 away from the stop 3a, as shown in FIG. 2 will interengage the rib portions 16a, 16b with the undercut regions 15 in the flange portions 13a and 13b respectively in a "dovetailed" manner to retain the handle members slidably assembled together as an integrated or composite handle.

The undercut region 15 of each proximal flange portion 13a is provided with serrations or teeth 18 (see FIG. 3a) which are resiliently cooperable with the teeth 19 on the associated rib portion 16a to releasably lock the handle members against unintentional relative sliding movement. Between the, opposed flange portions 13a, the transverse web or base 13c of the "H" section channel in the depressor handle member 6 is provided with a transverse, convex, arcuate actuating portion or button 21. This actuating portion 21 is isolated from the adjoining regions of the web by a pair of transverse slots 21a (see FIGS. 1 and 3) which increase the resilience of the actuating portion 21 and flange portions 13a. The height of the side walls of the upper channel of the handle member 6 is increased in the region of the flange portions 13a by extensions forming ears or grips 23.

By manually resiliently depressing the arcuate actuating portion 21, and/or pinching and flexing the ears 23 towards each other, the flange portions 13a will be flexed apart to temporarily disengage the teeth 18 and 19 partially or completely, and allow sliding adjustment between the handle portions. The upper surface of the actuating portion 21, and/or at least the adjacent regions of the transverse web, are ribbed or serrated as shown at 32. This ribbing, and ribbing (not shown) in the channel in the handle member 3, improve the doctor's grip on the instrument and prevent slipping during handling and adjustment due to soiling of the handle members by various body fluids.

In use of the instrument, and referring to FIG. 1, in the first step of a vaginal inspection, the doctor uses one hand to hold the speculum handle member 3 and insert the speculum blade 2 between the mucous vaginal membranes. The other hand is used to hold the depressor handle member 6 and insert the depressor so that it is positioned correctly to seize the region to be examined and/or acted upon, e.g. the cervix and portio. The vagina is then dilated slightly as indicated at 7. The handle members are then swung together in the direction of the unlabelled arrow to bring the distal end of the depressor handle member 6 adjacent the stop 3a. This allows the flange portions 13a, 13b to align with and pass through the gaps 16c, 16d, and thus allow the handle member 3 to fit into the channel in the handle member 6. In this condition, the elements 2 and 5 are still relatively close together.

FIG. 2 illustrates the second step of a vaginal inspection. The depressor handle member 6 is axially advanced relative to the speculum handle member 3 to interlock the rib portions 16a, 16b and undercut regions 15 of the handle members in a dovetail fashion as previously explained. This is readily achieved by holding the assembled handle members in one (e.g. left) hand as shown, and depressing the arcuate web portions or button 21 with the thumb 10 (represented by the arrow 22 in FIG. 3a) to flex apart the flange portions 13a and separate the teeth 18, 19 whilst simultaneously urging the handle member 6 axially along the handle member 3 with the thumb. Instead of, or in addition to, depressing the actuating portion 21, the flange portions 23 may be flexed by pinching the ears 23 (represented by the arrows 24 in FIG. 3a) between the thumb 11 and index finger 12 of the other (right) hand as shown in broken lines in FIG. 2. When the actuating portion 21 and/or ears 23 are released, the flange portions 13a spring back, and the teeth 18, 19 interlock, immobilising the handle members, and holding the speculum and depressor blades 2, 5 at their required spacing.

It will thus be apparent that the handle member and blades 2, 5 can be readily slidably mutually adjusted in both linear directions. The doctor is thereby able to make any final adjustments to the vaginal instrument to achieve the best positioning for a surgical operation, and to reduce any discomfort felt by the patient. The doctor may then release his hold on the locked instrument, and thus use both hands to carry out the inspection and/or operation, after which the interlocked mechanism is released with a light touch, and the instrument is then removed and thrown away.

FIG. 4 also illustrates the design of the member 8 which is intermediate the blade or tongue 5 and the depressor handle member 6. For optimum vision and space, the intermediate handle member 8 is curved in an arcuate manner to the left (for right-handed doctors), or the right as indicated in broken lines (for left-handed doctors). For reasons of stability, the intermediate member 8 may also have an annular shape, the inner radius 25 of which should however be as large as possible in order to leave the vaginal opening unobstructed.

FIG. 1 and 4a also show the somewhat conical shape 26 of the foremost upper part of depressor tongue or blade 5 compared to the slight tapering of the central part 27. This makes it easier for the doctor to seize the cervix and similar organs.

Figure 5:
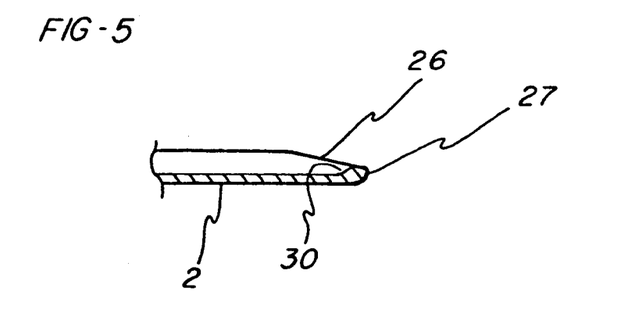
FIG. 5 illustrates in greater detail, the tip of a speculum element.

With reference to FIG. 5, in addition to the conical shape 26 and taper 27 similar to the foremost part of depressor tongue or blade shown in FIGS. 4 and 4a, the speculum tongue or blade is furthermore equipped with a small raised member 30 to enable the doctor to seize and/or place the projecting cervix on the blade.

Figure 6:
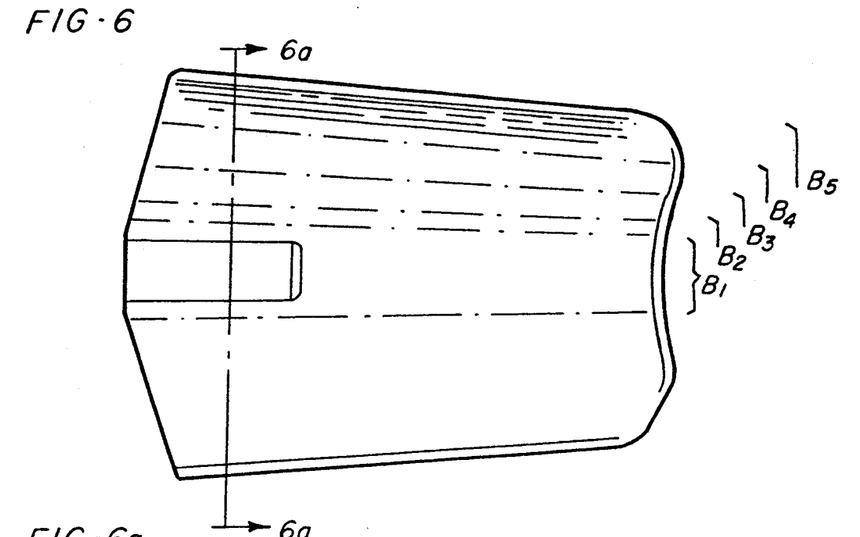
FIG. 6 illustrates a range of blade widths, in particular for interchangeable speculum elements.
Figure 6A:
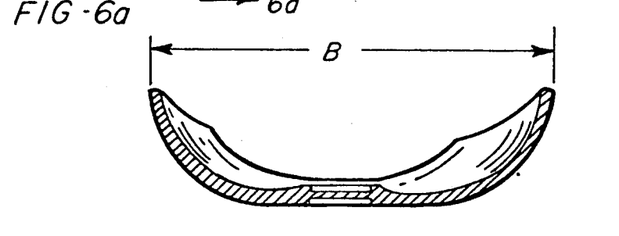
FIG. 6a is a cross-sectional view on the line 6a—6a in FIG. 6.

Instead of forming the speculum and depressor elements integrally with their associated handle members, one or both handle members may be adapted to receive separate elements. The dash-dot lines in FIG. 6b indicate, schematically, the different half-widths $B_1$ and $B_2$, etc., of a series of various tongues or blades 2 and 5 for use as the speculum and depressor elements respectively. The choice of instrument often depends on the age of the patient and whether she has given birth or not. Blade dimensions, especially the width (B), may thus vary greatly, for example from 20 mm to 100 mm. The manufacture of instruments with blade or tongues formed integrally with the speculum and depressor handle members may, from a mould manufacturing point of view, and even stockwise, prove unnecessarily expensive.

Figures 7, 7A, 7B:
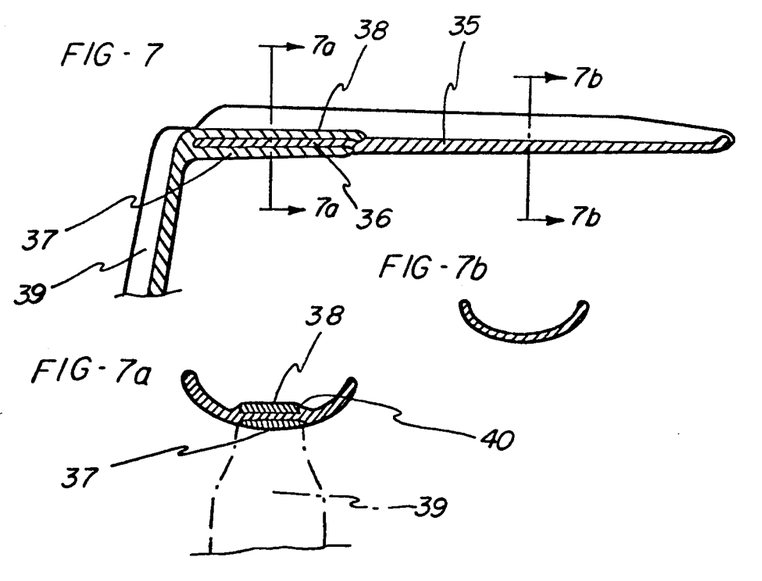
FIG. 7 illustrates optional blade sizes for interchangeable elements attachable to both the speculum and depressor handle members and FIGS. 7a and 7b are cross-sectional views taken, respectively, on the lines 7a—7a and 7b—7b in FIG. 7.

FIGS. 7 and 7a show a simple insertion arrangement 36 for enabling detachable tongues or blades 35 to be inserted into the speculum handle member. A similar attachment arrangement may additionally or alternatively be applied to the depressor handle member. Different methods of attachment may used, but it is, however, vital that the outer surface 37 of the holder is as smooth as possible in order to avoid injuring the mucous vaginal membranes. Towards the arcuate blade center 38 the blade thickness may be slightly increased as shown at 40 in order to obtain optimum stability The speculum and depressor elements, and in particular the handle members 3, 6, associated guide means (flanges 13, 14), associated retaining means (undercut regions 15 and rib portions 16) associated interlocking means (teeth 18, 19), laterally offset intermediate member 8, and/or blades or tongues 2, 5, may be formed from any appropriate material, for example, bent, stamped or folded or otherwise fabricated from metal, and/or moulded from a synthetic plastics material, or formed from combinations thereof.

It will be understood that various modifications may be made without departing from the scope of the present invention as defined in the appended claims.

For example, the speculum component or member, instead of or in addition to the depressor component or member, may incorporate a laterally offset intermediate member.

The blades or tongues 2, 5 may be of different lengths, for example, as viewed in FIG. 2, the depressor blade 5 may be shorter than the speculum blade 2 so that the free end of the latter projects beyond the free end of the former.

The locking means, for example teeth 18 and 19, may be arranged to be resiliently disengageable without the actuation of the actuating portion 21 or ears 23, simply by manually forcing one of the handle members axially relative to the other. The resilient ratchet or snap action of the teeth may be arranged to exert a relatively high resistance to closing movement of the depressor and speculum blades, whilst exerting a relatively low or negligible resistance to separational movement therebetween.

Although primarily intended for use as an instrument for vaginal inspection and/or exploration, the invention, for example one or more of the previously mentioned features, may be embodied in other types of instruments for other uses, whether medical, surgical or non-medical.

I claim:

1. An instrument for enabling the inspection and/or exploration of a body cavity or the like, comprising a first component, having a first elongate hand-grip member, and a first elongate body-engageable element, the first hand-grip member, in use, being connected to the first body-engageable element, and being adapted to be grasped in one hand for manipulation of the first body-engageable element, a second component, separable from the first component, having a second elongate hand-grip member, and a second elongate body-engageable element, the second hand-grip member, in use, being connected to the second body-engageable element, and being adapted to be grasped in one hand, independently of the first hand-grip member, for manipulation of the second body-engageable element independently of the first body-engageable element, one hand-grip member being releasably slidably receivable in a longitudinal substantially straight channel defined by the other hand-grip member with the cooperating surfaces of the channel and of said one hand-grip member forming guide means operable to constrain the hand-grip members to extend, and to be relatively manually displaceable, in a first common direction, along a substantially rectilinear path, to relatively adjust the separation between the first and second body - engageable elements, the guide means being associated with resilient locking means operable to releasably lock the hand-grip members in an adjusted position, the guide means also being associated with retaining means operable to retain the hand-grip members interconnected to form an integrated handle adapted to be grasped in one hand with the manipulation of both body-engageable elements, and the relative separational adjustment, being effected by said one hand, the side walls of the channel in said other hand-grip member, and the sides of said one hand-grip member with which the side walls are cooperable, being provided with said retaining means, which retaining means comprise longitudinally extending, internal undercut regions in the side walls in which longitudinally extending rib portions on the sides are slidably engageable, said undercut regions and rib portions being adapted to permit the hand-grip members to be assembled and disassembled when the body-engageable elements are located close together, each body-engageable element, in use, extending at an angle to its associated hand-grip member whereby, when the hand-grip members are interconnected, the body-engageable elements are constrained to extend generally in a second common direction, at an angle to said first common direction, with the first body-engageable element interposed between the second body-engageable element and the first hand-grip member in the direction of elongation of the integrated handle, and the second hand-grip member including an intermediate member, the second hand-grip member, in use, being connected to the second body-engageable element by the intermediate member, and the intermediate member being offset laterally relative to the body-engageable elements to provide access, in the direction of elongation of the elements, past the intermediate member to the space between the elements.

2. An instrument as claimed in claim 1, wherein said one hand-grip member is the first hand-grip member, and said other hand-grip member is the second hand-grip member.

3. An instrument as claimed in claim 1, wherein the cooperable surfaces of the undercut regions and rib portions are inclined so as to interlock in a dovetail manner.

4. An instrument as claimed in claim 1, wherein at least one of the channel walls has a wall portion provided with locking means, cooperable with locking means associated with an opposed surface of said one hand-grip member to lock the hand-grip members, when assembled together, against relative sliding movement, the wall portion being resiliently manually deflectable to at least partially disengage the locking means and permit sliding movement between the hand-grip members and corresponding adjustment of the spacing between the body-engageable elements.

5. An instrument as claimed in claim 4, wherein said other hand-grip member is provided with integral actuation means connected to the deflectable wall portion, the actuation means being manually displaceable to deflect the wall portion and disengage the locking means.

6. An instrument as claimed in claim 5, wherein each hand-grip member has a proximal end adjacent its associated body-engageable element and a distal end remote from the latter, and wherein the side walls of the channel adjacent the proximal end of said other hand-grip member are provided with opposed deflectable wall portions.

7. An instrument as claimed in claim 5, wherein the actuation means includes a manually depressible, resilient, web portion in the base wall of the channel.

8. An instrument as claimed in claim 7, wherein the actuation means includes manually deflectable extensions of the channel side walls in the region of the wall portions.

9. An instrument as claimed in claim 1, wherein the channel side walls are longitudinally interrupted to provide discrete proximal wall portions adjacent the associated body-engageable element, and discrete distal wall portions remote from the latter.

10. An instrument as claimed in claim 9, wherein each side of said one hand-grip member is provided with a proximal rib portion and an intermediate rib portion longitudinally spaced from the proximal rib portion and from the distal end of the hand-grip member by intermediate and distal gaps, the discrete proximal and distal channel wall portions of said other hand-grip member being alignable and cooperable with the intermediate and distal gaps, when the body-engageable elements are located close together, to permit the hand-grip members to be assembled or disassembled in directions corresponding generally to the longitudinal direction of the body-engageable elements.

11. An instrument as claimed in claim 10, including stop means for mutually longitudinally locating the hand-grip members to align the proximal and distal channel wall portions with the intermediate and distal gaps to facilitate assembly and disassembly of the hand-grip members.

12. An instrument as claimed in claim 4, wherein the locking means comprise at least one tooth associated with the wall portion of said other hand-grip member, cooperable selectively with a plurality of longitudinally distributed teeth associated with the opposed surface of said one hand-grip member.

13. An instrument as claimed in claim 4, wherein said one hand-grip member is formed with a longitudinally extending channel opening outwardly away from the channel in said other hand-grip member.

14. An instrument as claimed in claim 1, wherein the intermediate member extends along a generally arcuate path between said other hand-grip member and body-engageable element.

15. An instrument as claimed in claim 4, wherein the hand-grip members and their associated guide means, locking means, retaining means and intermediate member, are moulded integrally from a resilient synthetic plastics material.

16. An instrument as claimed in claim 1, wherein the body-engageable elements are interchangeably connectable to the hand-grip members.

17. An instrument for use in vaginal inspection and/or exploration, as claimed in claim 1, wherein the first component is a speculum component and the second component is a depressor component.

18. An instrument for expanding a body cavity and for maintaining the body cavity in an expanded condition, comprising a first component, having a first elongate handle member which, in use, is connected to a first elongate body-engageable element, a second component, having a second elongate handle member which, in use, is connected to a second elongate body-engageable element, one handle member being releasably slidably receivable in a longitudinal channel defined by the other handle member with the cooperating surfaces of the channel and of said one handle member forming guide means operable to constrain the handle members to extend, and to be relatively manually displaceable, in a first common direction, to relatively adjust the separation between the first and second body - engageable elements, the guide means being associated with resilient locking means operable to releasably lock the handle members in an adjusted position, the guide means also being associated with retaining means operable to retain the handle members interconnected to form an integrated handle, each body-engageable element, in use, extending at an angle to its associated handle member whereby, when the handle members are interconnected, the body-engageable elements are constrained to extend generally in a second common direction, at an angle to said first common direction, with the first body-engageable element interposed between the second body-engageable element and the first handle member in the direction of elongation of the integrated handle, the second handle member including an intermediate member, the second handle member, in use, being connected to the second body-engageable element by the intermediate member, and the intermediate member being offset laterally relative to the body-engageable elements to provide access, in the direction of elongation of the elements, past the intermediate member to the space between the elements, the side walls of the channel in said other handle member, and the sides of said one handle member with which the side walls are cooperable, being provided with said retaining means, which retaining means comprise longitudinally extending, internal undercut regions in the side walls in which longitudinally extending rib portions on the sides are releasably slidably engageable, the channel side walls being longitudinally interrupted to provide discrete proximal wall portions adjacent the associated body-engageable element, and discrete distal wall portions remote from the latter, and each side of said one handle member being provided with a proximal rib portion and an intermediate rib portion longitudinally spaced from the proximal rib portion and from the distal end of the handle member by intermediate and distal gaps, the discrete proximal and distal channel wall portions of said other handle member being alignable and cooperable with the intermediate and distal gaps, when the body-engageable elements are located close together, to permit the handle members to be assembled or disassembled in directions corresponding generally to the longitudinal direction of the body-engageable elements.

19. An instrument as claimed in claim 18, including stop means for mutually longitudinally locating the handle members to align the proximal and distal channel wall portions with the intermediate and distal gaps to facilitate assembly and disassembly of the handle members.

20. An instrument for expanding a body cavity and for maintaining the body cavity in an expanded condition, comprising, a first component, having a first elongate handle member which, in use, is connected to a first elongate body-engageable element, a second component, having a second elongate handle member which, in use, is connected to a second elongate body-engageable element, one handle member being releasably slidably receivable in a longitudinal channel defined by the other handle member with the cooperating surfaces of the channel and of said one handle member forming guide means operable to constrain the handle members to extend, and to be relatively manually displaceable, in a first common direction, to relatively adjust the separation between the first and second body-engageable elements, the guide means being associated with resilient locking means operable to releasably lock the handle members in an adjusted position, the guide means also being associated with retaining means operable to retain the handle members interconnected to form an integrated handle, each body-engageable element, in use, extending at an angle to its associated handle member whereby, when the handle members are interconnected, the body-engageable elements are constrained to extend generally in a second common direction, at an angle to said first common direction, with the first body-engageable element interposed between the second body-engageable element and the first handle member in the direction of elongation of the integrated handle, the second handle member including an intermediate member, the second handle member, in use, being connected to the second body-engageable element by the intermediate member, and the intermediate member being offset laterally relative to the body-engageable elements to provide access, in the direction of elongation of the elements, past the intermediate member to the space between the elements, the side walls of the channel in said other handle member, and the sides of said one handle member with which the side walls are cooperable, being provided with said retaining means, which retaining means comprise longitudinally extending, internal undercut regions in the side walls in which longitudinally extending rib portions on the sides are releasably slidably engageable, at least one of the channel walls having a wall portion provided with locking means, cooperable with locking means associated with an opposed surface of said one handle member to lock the handle members, when assembled together, against relative sliding movement, the wall portion being resiliently manually deflectable to at least partially disengage the locking means and permit sliding movement between the handle members and corresponding adjustment of the spacing between the body-engageable elements, and wherein said one handle member is formed with a longitudinally extending channel opening outwardly away from the channel in said other handle member.

* * * * *